United States Patent [19]

Counsell et al.

[11] 4,048,297

[45] Sept. 13, 1977

[54] NOVEL QUATERNARY AMMONIUM SALTS, COMPOSITIONS AND METHODS FOR THEIR USE

[75] Inventors: Raymond E. Counsell, Ann Arbor; Terry Ta-Jen Yu, Warren, both of Mich.

[73] Assignee: The Regents of the University of Michigan, Ann Arbor, Mich.

[21] Appl. No.: 642,036

[22] Filed: Dec. 18, 1975

Related U.S. Application Data

[63] Continuation of Ser. No. 526,830, Nov. 25, 1974, abandoned.

[51] Int. Cl.$^2$ .................... A61K 29/00; A61K 43/00; C07C 87/30; G01T 1/161
[52] U.S. Cl. ........................................ 424/1; 128/2 A; 250/303; 260/567.6 M; 424/9
[58] Field of Search ............................... 424/1, 9, 329; 260/567.6 R, 567.6 M; 250/303; 128/2 A

[56] References Cited

U.S. PATENT DOCUMENTS 3,834,867  9/1974  Matter et al. ............ 260/567.6 M X

OTHER PUBLICATIONS

Kojima et al., Chemical Abstracts, vol. 79, No. 3, July 23, 1973, Abstract No. 15079n.
Boura et al., Brit. J. Pharmacol., vol. 17, 1961, pp. 92–100.
Carr et al., Clinical Pharmacology and Therapeutics, vol. 14, 1973, p. 132.
Counsell et al., J. Med. Chem., vol. 16, No. 9, 1963, pp. 1038–1040.

*Primary Examiner*—Benjamin R. Padgett
*Assistant Examiner*—Christine M. Nucker
*Attorney, Agent, or Firm*—John A. Dhuey

[57] ABSTRACT

Para-iodobenzyltrimethylammonium iodide is useful as an intermediate in the manufacture of the corresponding compounds wherein the para-iodo atom is enriched with an $^{123}$iodine, $^{125}$iodine or $^{131}$iodine isotope. These radio-iodinated derivatives are valuable adrenal scanning agents in consequence of their propensity to localize in the adrenal gland. Moreover, their ability to bind to catecholamine storage sites accounts for their ability to localize in tissue having a large supply of adrenergic nerves such as spleen and sympathetic ganglia. When injected directly into the cerebrospinal fluid, they concentrate in the choroid plexus and in adrenergic innervated tissues such as the substantia nigra.

7 Claims, No Drawings

NOVEL QUATERNARY AMMONIUM SALTS, COMPOSITIONS AND METHODS FOR THEIR USE

This is a continuation of application Ser. No. 526,830, filed Nov. 25, 1974, now abandoned.

The present invention is concerned with novel chemical compounds belonging to the class of quaternary ammonium salts, which compounds are represented by the following structural formula

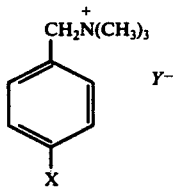

wherein X represents an iodine atom or an iodine atom enriched with an isotope selected from the group consisting of $^{123}$iodine, $^{125}$iodine and $^{131}$iodine, and Y represents a pharmaceutically acceptable anion. The pharmaceutically acceptable anions encompassed by the foregoing structural formula are typified by the halide ions, i.e. chloride, bromide, fluoride, iodide, and the sulfate, phosphate, benzenesulfonate, p-toluenesulfonate and alkylsulfate ions.

The iodine isotope enriched compounds are particularly useful as adrenal scanning agents in view of their propensity for localization in adrenergically-innervated tissues, especially the medulla of the adrenal gland.

The radioiodinated compounds of this invention fulfill a long sought need for agents which will selectively localize in the adrenal medulla to a degree rendering them suitable for use as scanning agents for the purpose of detecting abnormal adrenal conditions, e.g., neural crest tumors such as pheochromacytoma and neuroblastoma. Their ability to concentrate in the choroid plexus and other sites in the central nervous system after intrathecal administration renders them useful in cisternography for diagnosing diseases of central origin. No agent of this type is currently available.

Closely relates studies have led to agents useful for adrenal scanning, but in this case an ability to concentrate in the adrenal cortex was the determining factor. For example, the use of steroid molecules as radioiodine carriers was investigated by Counsell et al., Steroids, 11, 817 (1968). Radioiodinated progesterone and pregnenolone were systhesized, but found to be unsuitable as a result of rapid in vivo deiodination when administered to dogs, resulting in localization of the radioactivity in the thyroid gland. An unsuccessful attempt to find a suitable agent was reported by Nagai et al., J. Nucl. Med., 9 576 (1968). Thus, radioiodination of cholesterol with $^{131}$sodium iodide afforded a product which deiodinated in vivo in mice thus resulting in low adrenal/liver radionuclide ratios. More satisfactory results were obtained with the radioiodinated 19-iodo cholesterols reported by Counsell et al, Steroids, 16, 317 (1970) and Beierwaltes et al., J. Amer. Med. Assoc., 216, 275 (1971). Their clinical use in a diagnosis of unilateral adrenocortical adenoma, primary aldosterone adenoma, Cushing's syndrome and adrenal remnants has been subsequently described in the literature by various workers. Since these agents localize in the adrenal cortex, however, they are not suitable for detection of abnormalities in the inner structure, i.e., in the medulla, of the adrenal glands.

Tumors which can arise from the adrenal medulla are typified by pheochromocytoma and neuroblastoma. In a search for agents which would localize in the medulla, andthus be suitable as scanning agents for the detection of abnormalities, e.g. he aforementioned tumors, Morales et al., J. Nucl. Med., 8, 800 (1967) prepared and testedin dogs various $^{14}$carbon labeled catecholamines, catecholamimeprecursors, p-tyramine, and β-phenethylamine. Both $^{14}$carbon dopamine and $^{14}$carbon p-tyramine were selectively taken out by the adrenal medulla, while $^{14}$carbon β-phenethylamine showed no such predilection. These derivatives, however, suffer from the disadvantages characteristic of β-ray emitting radionuclides, e.g. β-radiation under normal circumstances is unsuitable for external scanning or organs or tumors since such radiation is readily absorbed by surrounding tissue. γ-Ray emitting nuclides, as represented by those containing the radioactive isotopes of iodine, are highly advantageous in view of the enhanced ability of those rays to penetrate animal tissue. The radioiodinated compounds of the present invention thus are preferred agents for scanning of the adrenal medulla.

The compounds of this invention are conveniently manufactured by a two-step process, which comprises the reaction of a p-iodobenzyl halide, e.g., p-iodobenzyl chloride, p-iodobenzyl bromide; with dimethylamine followed by quaternization of the resulting tertiary amine by reaction with methyl iodide. Synthesis of the radiolabelled derivatives is achieved by exchange with the appropriate iodide nuclide in the form of its alkaline metal salt. The exchange may be conducted at either the tertiary amine of the quaternary stage. In the latter instance, the initial product is subsequently treated at room temperature with non-radioactive sodium iodide in order to remove the radioactive isotopes from the iodide anion.

The novel compositions of this invention consist of one of the aforementioned active ingredients combined with a pharmaceutically acceptable carrier. These compositions can be administered either orally or parenterally. For oral administration, tablets, lozenges, capsules, dragees, pills or powders are suitable, while aqueous solutions, non-aqueous solutions or suspensions are appropriate for parenteral administration. Acceptable pharmaceutical carriers are exemplified by gelatin capsules, sugars such a lactose or sucrose, starches such as corn starch or potato starch, celulose derivatives such as sodium carboxy methyl cellulose, ethyl cellulose, methyl cellulose or cellulose acetate phthalate, gelatin, talc, calcium phosphate such as dicalcium phosphate or tricalcium phosphate, sodium sulfate, calcium sulfate, polyvinyl pyrrolidone, acacia, polyvinyl alcohol, steric acid, alkaline earth metal stearates such as magnesium stearate, vegetable oils such as peanut oil, cottonseed oil, sesame oil, olive oil, corn oil, or acetobromo, water, agar, alginic acid, benzyl alcohol, isotonic saline and phosphate buffer solutions as well as other non-toxic compatible substances.

The amount of radiolabeled compound to be administered to the mammal is that amount which will enable effective visualization of the adrenal medulla. The amount will vary with the method of administration, the particular compound used and the nature of the subject A recommended dosage for parenteral, e.g., intravenous or intramuscular administration, is 10–30 MCi/Kg of body weight.

The invention will appear more fully from the examples which follow. These examples are given by way of illustration only and are not to be construed as limiting the invention either in spirit or in scope as many modifications both in materials and methods will be apparent to those skilled in the art. In the following examples, temperatures are given in degrees Centigrade (° C.) and quantities of materials in parts by weight unless otherwise noted.

EXAMPLE 1

To a solution of 9 parts of p-iodobenzyl bromide in 25 parts by volume of benzene is added dropwise with stirring 25 parts by volume of a 20% dimethylamine in benzene solution. The reaction mixture is kept at room temperature for about 16 hours, then is heated at the reflux temperature for about 1 hour. The solvent and unreacted dimethylamine are removed by distillation under reduced pressure and the resulting residue extracted with ether. The insoluble dimethylamine hydrobromide is removed by filtration and the filtrate is washed with water, dried over anhydrous sodium sulfate and concentrated to dryness under reduced pressure. The resulting residue is dissolved in methanolic hydrogen chloride and the resulting precipitated salt is purified by recrystallization from methanol-ether to afford p-iodobenzyl dimethylaminehydrochloride, melting at about 213°–214°.

EXAMPLE 2

A solution containing 0.075 part of p-iodobenzyl dimethylaminehydrochloride and 5 millicuries of sodium $^{125}$iodide in 4 parts by volume of ammonium hydroxide is heated at reflux temperature in an atmosphere of nitrogen for about 24 hours, then is allowed to cool and poured into 20 parts by volume of 10% aqueous sodium hydroxide. The resulting alkaline solution is extracted with chloroform and that extract is washed with water, dried over anhydrous sodium sulfate and stripped of solvent, thus affording the radioiodinated amine salt having a specific activity of 30 microcuries/milligram. Analysis of the product by thin layer chromatography using ether as the solvent reveals a single spot, having an $R_f$ value of 0.43, while the use of a 1:1 benzene:ether solvent system produced a single spot having an $R_f$ value of 0.32. These peaks are coincident with the single radioactive peak appearing on the radiochromatogram.

The latter radioiodinated amine salt is dissolved in 1 part by volume of methanol and 0.04 part of methyliodide is added. The resulting mixture is stirred at room temperature for about 2 hours, at the end of which time the solvent is removed by evaporation. Recrystallization of the resulting residue from methanol-ether affords p-iodobenzyltrimethylammonium iodide enriched in the $^{125}$iodine isotope, and possessing a specific activity of 24 microcuries/milligram. Analysis of that product using either a 1:2 methanol:chloroform or 1:2 ethanol:chloroform solvent system affords a single peak coincident with the peak displayed on the radiochromatogram.

EXAMPLE 3

Radioiodinated compounds are given by intravenous or subcutaneous injection to immature male Sprague-Dawley albino rats weighing 175–200 g. The dose administered is approximately 50 millicuries per rat and the vehicle used is isotonic saline. Groups of 3 animals are killed by exsanguination through the ventricle 2, 6 and 18 hours post-injection. The major organs, such as liver, kidney, lung, spleen, auricle, and ventricle, are excised, weighed and homogenized. These organs are washed thoroughly with isotonic saline to remove blood, dried and minced with scissors and placed in a homogenizer tube containing 20 ml. water in the case of liver and 2 ml. of water in the case of the other major organs. Homogenates are not prepared for small organs such as adrenal and thyroid. Several samples of homogenates, heparinized blood and plasma specimens and entire adrenal, thyroid and other tissue samples, such as fat and muscle, are placed in scintillation counting vials. To each vial 0.3 of 2.5 M sodium hydroxide solution is added and left overnight and then heated for at least 10 minutes at 60° in a water bath to complete the digestion. The vials are allowed to cool and 0.7 ml. of 1.1 M acetic acid, 0.05 ml. of 30% hydrogen peroxide and 10 ml. of Aquasol (xylene based liquid scintillation counting solution obtained from New England Nuclear, Boston, Mass.) cocktail are added successively to each vial and the contents shaken using a vortex mixer. The vials are kept in a cool, dark place for at least 4 hours before counting. Radioactivity is assayed in a Beckman LS-200 liquid scintillation spectrometer. Sufficient counts are accumulated to reduce the probable error of counting to less than 5%. All counts are corrected for quenching by using the $^{125}$iodine-quenched standard curves.

What is claimed is:
1. A compound of the formula

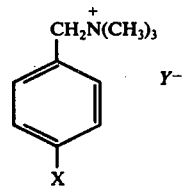

wherein X is iodine, $^{123}$iodine, $^{125}$iodine or $^{131}$iodine and $Y^-$ represents a pharmaceutically acceptable anion.

2. As in claim 1, a compound of the formula

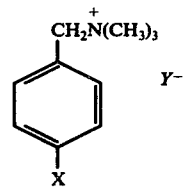

wherein X is iodine, $^{123}$iodine, $^{125}$iodine or $^{131}$iodine and $Y^-$ represents chloride, bromide, iodide, sulfate, p-toluenesulfonate or phosphate.

3. As in claim 1, a compound of the formula

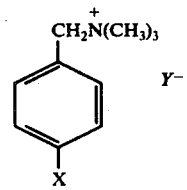

wherein X is $^{123}$iodine, $^{125}$iodine, or $^{131}$iodine and $Y^-$ represents iodide.

4. As in claim 1, the compound which is paraiodobenzyltrimethylammonium iodide.

5. As in claim 1, the compound which is paraiodobenzyltrimethylammonium iodide enriched in the $^{125}$iodine isotope.

6. A method for visualizing adrenergic-innervated tissues of mammels which comprises administering to the mammal an effective amount of a compound of the formula

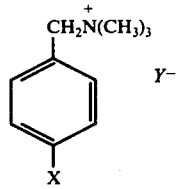

wherein X is $^{123}$iodine, $^{125}$iodine or $^{131}$iodine and Y$^-$ is a pharmaceutically acceptable anion.

7. A method as in claim 6, wherein X is $^{125}$iodine and Y$^-$ is iodide.

* * * * *